US012171932B2

(12) United States Patent
Dwyer et al.

(10) Patent No.: US 12,171,932 B2
(45) Date of Patent: Dec. 24, 2024

(54) MEDICAL NEBULIZER FOR FAST DRUG DELIVERY

(71) Applicant: Medline Industries, LP, Springfield, IL (US)

(72) Inventors: Daniel P. Dwyer, Cary, NC (US); Erin Hillocks, Chapel Hill, NC (US)

(73) Assignee: Medline Industries, LP, Springfield, IL (US)

( * ) Notice: Subject to any disclaimer, the term of this patent is extended or adjusted under 35 U.S.C. 154(b) by 0 days.

(21) Appl. No.: 17/525,627

(22) Filed: Nov. 12, 2021

(65) Prior Publication Data

US 2022/0062566 A1 Mar. 3, 2022

Related U.S. Application Data

(63) Continuation of application No. 16/042,472, filed on Jul. 23, 2018, now abandoned.
(Continued)

(51) Int. Cl.
*A61M 11/04* (2006.01)
*A61M 11/00* (2006.01)
(Continued)

(52) U.S. Cl.
CPC .......... *A61M 11/04* (2013.01); *A61M 11/001* (2014.02); *A61M 11/002* (2014.02);
(Continued)

(58) Field of Classification Search
CPC ................ A61M 11/00–08; A61M 15/00–085
(Continued)

(56) References Cited

U.S. PATENT DOCUMENTS 3,762,409 A    10/1973   Lester
4,429,835 A *   2/1984   Brugger ............... A61M 11/002
                                                239/338
(Continued)

FOREIGN PATENT DOCUMENTS

EP      0170715 A1    2/1986
GB      2347870 A     9/2000
JP      H02116379 A   5/1990

OTHER PUBLICATIONS

PCT International Search Report and Written Opinion, PCT/US2018/043269, Oct. 1, 2018, 11 pages.
(Continued)

*Primary Examiner* — Valerie L Woodward
*Assistant Examiner* — Paige Kathleen Bugg
(74) *Attorney, Agent, or Firm* — Quarles & Brady LLP (57) ABSTRACT

A nebulizer is provided to atomize a liquid medication for rapid delivery of an aerosol spray to a user via inhalation. The nebulizer includes a jar having a compressed gas passage. A jet cooperates with the jar and has a jet orifice through which the liquid medication and the compressed gas are discharged to form an aerosol flow. The cap is connected to the jar to define an inner chamber. The cap includes an entrainment port for ambient room air, and a chimney in fluid communication with the entrainment port and the inner chamber. A deflector base having an impingement member is located adjacent to the entrainment chimney and is spaced below an opening thereof by a predetermined distance to provide a flow of the ambient room air to be entrained in the aerosol flow in order to enhance nebulization speed while maintaining a desired aerosol particle size.

23 Claims, 4 Drawing Sheets

Related U.S. Application Data (60) Provisional application No. 62/540,225, filed on Aug. 2, 2017.

(51) Int. Cl.
*A61M 11/06* (2006.01)
*A61M 15/00* (2006.01)

(52) U.S. Cl.
CPC .......... *A61M 11/06* (2013.01); *A61M 15/002* (2014.02); *A61M 15/0086* (2013.01)

(58) Field of Classification Search
USPC .................................................. 128/200.21
See application file for complete search history.

(56) References Cited

U.S. PATENT DOCUMENTS

| | | | |
|---|---|---|---|
| RE33,642 E | 7/1991 | Lester | |
| 5,054,477 A | 10/1991 | Terada et al. | |
| 5,209,225 A * | 5/1993 | Glenn .................. | B05B 7/2435 239/338 |
| 5,241,954 A * | 9/1993 | Glenn .................. | B05B 7/0012 239/338 |
| 5,312,046 A | 5/1994 | Knoch et al. | |
| 5,579,757 A | 12/1996 | McMahon et al. | |
| 5,584,285 A | 12/1996 | Salter et al. | |
| 5,586,550 A | 12/1996 | Ivri et al. | |
| 5,687,912 A * | 11/1997 | Denyer .................. | A61M 11/06 239/338 |
| 5,738,086 A | 4/1998 | McMahon et al. | |
| 5,758,637 A | 6/1998 | Ivri et al. | |
| 5,823,179 A | 10/1998 | Grychowski et al. | |
| 5,875,774 A | 3/1999 | Clementi et al. | |
| 5,938,117 A | 8/1999 | Ivri | |
| 6,014,970 A | 1/2000 | Ivri et al. | |
| 6,085,740 A | 7/2000 | Ivri et al. | |
| 6,085,741 A | 7/2000 | Becker | |
| 6,338,443 B1 * | 1/2002 | Piper .................... | A61M 11/002 239/338 |
| 6,530,370 B1 | 3/2003 | Heinonen | |
| 6,539,937 B1 | 4/2003 | Haveri | |
| 6,550,472 B2 | 4/2003 | Litherland et al. | |
| 6,595,203 B1 * | 7/2003 | Bird .................. | A61M 16/0006 239/338 |
| 6,651,650 B1 | 11/2003 | Yamamoto et al. | |
| 6,769,626 B1 | 8/2004 | Haveri | |
| 6,796,513 B2 | 9/2004 | Fraccaroli | |
| 6,851,626 B2 | 2/2005 | Patel et al. | |
| 7,201,167 B2 | 4/2007 | Fink et al. | |
| 7,267,120 B2 | 9/2007 | Rustad et al. | |
| 7,559,491 B1 | 7/2009 | Chang | |
| 7,581,718 B1 * | 9/2009 | Chang .................. | B05B 7/0012 261/78.2 |
| 7,726,306 B2 | 6/2010 | Addington et al. | |
| 7,841,335 B2 | 11/2010 | Harrington et al. | |
| 7,905,228 B2 | 3/2011 | Blacker et al. | |
| 7,980,247 B2 | 7/2011 | Boehm et al. | |
| 8,006,698 B2 | 8/2011 | Boehm et al. | |
| 8,113,194 B2 | 2/2012 | Boehm et al. | |
| 8,336,545 B2 | 12/2012 | Fink et al. | |
| 8,342,171 B2 | 1/2013 | Boehm et al. | |
| 8,397,712 B2 | 3/2013 | Foley et al. | |
| 8,539,951 B1 | 9/2013 | Meyer et al. | |
| 8,596,263 B2 | 12/2013 | Piper | |
| 8,603,439 B2 | 12/2013 | Montgomery | |
| 8,616,195 B2 | 12/2013 | Power et al. | |
| 8,636,983 B2 | 1/2014 | Montgomery | |
| 8,636,984 B2 | 1/2014 | Montgomery | |
| 8,701,658 B2 | 4/2014 | Mazela et al. | |
| 8,820,323 B2 | 9/2014 | Montgomery | |
| 8,844,520 B2 | 9/2014 | Foley et al. | |
| 8,945,605 B2 | 2/2015 | Boucher et al. | |
| 9,119,930 B2 | 9/2015 | Kreutzmann et al. | |
| 9,205,050 B2 | 12/2015 | Charan et al. | |
| 9,351,929 B2 | 5/2016 | Charan et al. | |
| 9,351,930 B2 | 5/2016 | Charan et al. | |
| 9,352,114 B2 | 5/2016 | Mazela et al. | |
| 9,364,618 B2 | 6/2016 | Blacker et al. | |
| 9,504,794 B2 | 11/2016 | Esaki et al. | |
| 9,522,242 B2 | 12/2016 | Esaki et al. | |
| 9,539,407 B2 | 1/2017 | Varga et al. | |
| 9,539,408 B2 | 1/2017 | Pevler | |
| 10,786,638 B2 * | 9/2020 | Alizoti .............. | A61M 15/0093 |
| 2002/0157663 A1 * | 10/2002 | Blacker .................. | A61M 11/00 128/200.21 |
| 2003/0127538 A1 | 7/2003 | Patel et al. | |
| 2003/0140921 A1 | 7/2003 | Smith et al. | |
| 2003/0192962 A1 * | 10/2003 | Fraccaroli ............. | B05B 7/2435 239/524 |
| 2004/0031485 A1 * | 2/2004 | Rustad .................. | A61M 11/00 128/200.14 |
| 2005/0011514 A1 | 1/2005 | Power et al. | |
| 2005/0139211 A1 | 6/2005 | Alston et al. | |
| 2005/0199236 A1 | 9/2005 | Fink et al. | |
| 2005/0205089 A1 | 9/2005 | Fink et al. | |
| 2008/0054099 A1 * | 3/2008 | Giroux .................. | B05B 7/2429 96/4 |
| 2009/0272377 A1 * | 11/2009 | Piper, II ............... | A61M 11/002 128/200.18 |
| 2010/0126502 A1 | 5/2010 | Fink et al. | |
| 2010/0147292 A1 * | 6/2010 | Hamaguchi ........... | A61M 11/06 128/200.23 |
| 2011/0114090 A1 * | 5/2011 | Piper .................. | A61M 15/0091 128/200.23 |
| 2012/0125326 A1 | 5/2012 | Boehm et al. | |
| 2012/0227735 A1 * | 9/2012 | Abate ................ | A61M 15/0015 128/200.14 |
| 2012/0247462 A1 | 10/2012 | Charan et al. | |
| 2014/0000597 A1 * | 1/2014 | Korneff .................. | A61M 11/06 128/203.12 |
| 2014/0048062 A1 * | 2/2014 | Faram .................. | A61M 15/0016 128/200.14 |
| 2014/0116427 A1 | 5/2014 | Pevler | |
| 2014/0182583 A1 | 7/2014 | Wondka et al. | |
| 2015/0114504 A1 | 4/2015 | Cecka et al. | |
| 2016/0158467 A1 * | 6/2016 | Porteous ................ | A61M 11/06 128/200.21 |
| 2016/0317562 A1 | 11/2016 | Charan et al. | |
| 2018/0008789 A1 * | 1/2018 | Alizoti .............. | A61M 15/0016 |
| 2018/0161531 A1 * | 6/2018 | Costella ............ | G01N 15/0227 |
| 2019/0192790 A1 * | 6/2019 | Toddywala ....... | A61M 15/0018 |

OTHER PUBLICATIONS

European Patent Office, Extended Search Report, Application No. 18840536.9, Mar. 25, 2021, 9 pages.

* cited by examiner

MEDICAL NEBULIZER FOR FAST DRUG DELIVERY

CROSS-REFERENCE TO RELATED APPLICATIONS

This application is a continuation of U.S. patent application Ser. No. 16/042,472 filed Jul. 23, 2018, which claims priority to U.S. Provisional Patent Application No. 62/540,225 filed Aug. 2, 2017, the content of which is incorporated herein by reference in its entirety.

FIELD OF THE DISCLOSURE

The present disclosure relates generally to an aerosol delivery device, and more particularly, to a medical nebulizer configured to rapidly nebulize liquid medicament into an aerosol spray for inhalation by a user.

BACKGROUND

Medical nebulizers are used to aerosolize a liquid medicament for inhalation by a user. The aerosol is produced via the nebulization process by dispersing fine droplets of the liquid medicament into a flow stream of gas. The nebulized medicament can then be delivered into the airways of the user's lungs, which can be very useful in medical treatments due to the high permeability of the lungs. Medications inhaled into the lungs are therefore readily able to enter the user's bloodstream for dispersion throughout the rest of the user's body.

The medicated aerosol particles produced from a medical nebulizer must be sufficiently sized in order to provide safe and effective treatment to a user. Aerosol particles having an aerodynamic diameter between 1 and 5 micrometers are typically considered inhalable by a user. Many conventional medical nebulizers produce aerosol particles having an aerodynamic diameter that is less than 2 micrometers, which results in the deposition of the particles within the alveoli of the user's lungs. Other conventional medical nebulizers produce aerosol particles having an aerodynamic diameter that is over 5 micrometers, which results in the deposition of particles on the surface of the upper respiratory airways instead of reaching the lungs. The ideal respirable particle size range of aerosol particles is 1 micrometer to 5 micrometers in order to ensure deposition of medicated aerosol particles within the lower airways of a user upon inhalation.

A fast nebulization rate is often desired in order to yield a short overall treatment time for the user and maximize clinician workflow. However, conventional nebulizers that rapidly produce aerosol fail to maintain a beneficial particle size distribution of the aerosolized medicament. This is because increasing the nebulization rate for such conventional nebulizers results in aerosol particles that are often too large to be safely and effectively inhaled by a user. Large variances exist in the nebulization rate of conventional nebulizers, as well as the corresponding respirable size of the aerosol particles produced by conventional nebulizers.

Moreover, while some conventional nebulizers entrain room air during the nebulization process, such entrainment requires effort by the user to breath in the room air through the nebulizer. Relying on user effort to enhance the flow of air into the nebulizer can have varying levels of effectiveness since such user effort is dependent on the health condition of the user, including the user's lung capacity and stamina. Thus, users having poor health are often not able to effectively entrain a sufficient amount of room air into such conventional nebulizers. Additionally, users who rely on such conventional nebulizers that entrain room air during the nebulization process often experience deleterious effects, such as degrading the liquid consumption rate in the jar of the nebulizer, as well as spitting of the liquid medicament onto the user's hands and face via escape through an entrainment flow path.

Accordingly, there is a need for an improved nebulizer with a fast nebulization delivery rate for reducing user treatment time, thus helping user compliance and also enhancing clinician workflow efficiency. It is further desirable to quickly nebulize aerosol from a nebulizer while maintaining a beneficial aerosol particle size distribution between 1 and 5 micrometers for targeted lower airway deposition. Furthermore, there is a need for a medical nebulizer that doesn't cause deleterious effects, such as degrading the liquid consumption rate in the jar and spraying liquid medication out of the nebulizer through the entrainment flow path.

SUMMARY OF THE DISCLOSURE

The foregoing needs are met, to a great extent, by the present disclosure, wherein a nebulizer is configured to atomize a liquid medication for inhalation by a user. The nebulizer may comprise a jar defining a reservoir configured to hold the liquid medication, the jar defining a compressed gas passage configured to receive a flow of compressed gas. The compressed gas passage terminates in a jet orifice defined by the jar and the jet through which the liquid medication and the compressed gas are discharged to form an aerosol flow having the liquid medication entrained in the compressed gas. A cap is connected to the jar to define an inner chamber inside the nebulizer. The cap may comprise an entrainment port configured to provide an inlet for a flow of ambient room air; an entrainment chimney having a first opening in fluid communication with the entrainment port and a second opening in fluid communication with the inner chamber, the entrainment port and entrainment chimney together defining an entrainment pathway for the ambient room air; and a deflector base spaced below the second opening of the entrainment chimney by a predetermined distance to define at least one entrainment vent configured to provide a flow of the ambient room air into the inner chamber for enhancing nebulization speed of the nebulizer, such that the at least one entrainment vent is configured to rapidly entrain the ambient room air into the aerosol flow to form an ambient air-entrained aerosol spray for inhalation by the user.

According to another aspect of the disclosure, the cap may further comprise an impingement member extending from the deflector base and configured to further atomize particles in the aerosol flow and to prevent exhalation from the user from driving liquid medication out of the nebulizer through the entrainment pathway and out of the entrainment port.

According to another aspect of the disclosure, the at least one entrainment vent has a height greater than 0 inches and less than or equal to about 0.45 inches.

According to another aspect of the disclosure, the at least one entrainment vent has a height about 0.12 inches.

According to another aspect of the disclosure, a plurality of support fins connect the deflector base to the entrainment chimney.

According to another aspect of the disclosure, each of the at least one entrainment vents is provided between adjacent support fins.

According to another aspect of the disclosure, the impingement member includes a hemispherical surface.

According to another aspect of the disclosure, a center of the impingement member is aligned with an axis of the jet orifice.

According to another aspect of the disclosure, a flow axis of the entrainment port is substantially perpendicular to a flow axis of the entrainment chimney.

According to another aspect of the disclosure, the entrainment port is further configured to provide an inhalation pathway.

According to another aspect of the disclosure, the entrainment port is further configured to provide an exhalation pathway.

According to another aspect of the disclosure, the cap may further comprise an aerosol flow outlet port for outputting the aerosol flow to the user, the aerosol flow outlet port configured to connect to a user interface.

According to another aspect of the disclosure, the aerosol flow outlet port is configured to detachably connect to the user interface.

According to another aspect of the disclosure, the user interface is a mouthpiece or a breathing mask.

According to another aspect of the disclosure, the aerosol flow outlet port further includes a saliva catch configured to capture saliva from the mouth of the user during inhalation and exhalation.

According to another aspect of the disclosure, the cap is detachably connected to the jar.

According to another aspect of the disclosure, the deflector base may comprise a disk.

According to another aspect of the disclosure, the entrainment port is configured to connect to a PEEP valve or a filter.

According to another aspect of the disclosure, the entrainment chimney includes a longitudinal axis aligned with a longitudinal axis of the jet orifice.

According to another aspect of the disclosure, the entrainment chimney is generally tubular.

According to another aspect of the disclosure, particles in the aerosol flow have an aerodynamic diameter between 1 and 5 micrometers for targeted lower airway deposition.

According to another aspect of the disclosure, the nebulizer is configured to continuously nebulize the liquid medication during inhalation and exhalation of the user.

There has thus been outlined certain embodiments of the disclosure in order that the detailed description thereof herein may be better understood, and in order that the present contribution to the art may be better appreciated. There are additional embodiments of the disclosure that will be described below and which form the subject matter of the claims appended hereto.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

DETAILED DESCRIPTION

The disclosure will now be described with reference to the drawing figures, in which like parts are referred to with like reference numerals throughout. One or more embodiments in accordance with the present disclosure provide a breath enhanced medical nebulizer 10 for fast drug delivery, as shown throughout FIGS. 1-5. The nebulizer 10 is configured to aerosolize a liquid medication into an aerosol spray or mist for safe and effective inhalation by a user, such as a patient. The nebulizer 10 comprises a jar 20 configured to hold the liquid medication, a jet 30 configured to cooperate with the jar 20, and a cap 40 configured to detachably connect to the jar 20.

The jar 20 includes an outer surrounding wall 21 and defines a reservoir 22 configured to hold a liquid 24, such as a liquid medication. The jar further defines a compressed gas passage 26 configured to receive a flow of compressed gas. More particularly, the jar 20 comprises a compressed gas nozzle 23 having a first portion extending outside the surrounding wall 21 and a second portion extending into the reservoir 22. The compressed gas nozzle 23 comprises the compressed gas passage 26, which has a gas inlet 27 and a gas outlet 28. The jet 30 is detachably connected to the jar 20, and may further be configured to detachably connect to the second portion of the compressed gas nozzle 23 extending into the reservoir 22 by an interference fit. Additionally, the compressed gas nozzle 23 and the jet 30 may both be generally tubular in shape.

The jet 30 is configured to cooperate with the jar 20 such that a gap defining a fluid flow passage 34 is disposed between the jet 30 and the second portion of the compressed gas nozzle 23. The jet 30 includes a jet wall forming an internal cavity therein that is configured to receive the second portion of the compressed gas nozzle 23 extending into the reservoir 22. The fluid flow passage 34 comprises a vertical flow section and a horizontal flow section. The first portion of the compressed gas nozzle 23 having the compressed gas inlet 27 is configured to connect to a pressurized gas source or a gas supply tubing. The compressed gas passage 26 terminates in the gas outlet 28 such that an output of compressed gas is dispersed having an exit plane disposed substantially perpendicular to the fluid flow passage 34.

The jet 30 further comprises a jet orifice 32 located at an end of the internal cavity of the jet and provided in fluid communication with both the compressed gas passage 26 and the fluid flow passage 34. More particularly, the gas outlet 28 of the compressed gas passage 26 terminates in the jet orifice 32 through which the liquid medication and the compressed gas are discharged through to form an initial aerosol flow having the liquid medication entrained in the compressed gas.

The compressed gas outlet 28 and jet orifice 32 are configured to control the pressure-flow relationship of the nebulizer 10 by creating a venturi effect that causes a pressure drop of the compressed gas flowing through the gas outlet 28 and the jet orifice 32. Thus, during operation of the nebulizer 10, the compressed gas exits the gas outlet 28 and enters the jet orifice 32, creating a localized vacuum that draws liquid 24 from the fluid reservoir 22 into the fluid flow passage 34 due to negative pressure generated within the flow passage 34. The diameter of the gas outlet 28 may be approximately 0.010 to 0.025 inches. The jet orifice 32 is configured to ensure that a sufficient vacuum is maintained so that the liquid medication 24 drawn into the fluid flow passage 34 is further drawn through the jet orifice 32 and fully mixed with the compressed gas that is received from the gas outlet 28. This process atomizes the liquid medication, resulting in an aerosol flow being discharged from the jet orifice 32. The aerosol flow is subsequently entrained with a flow of ambient room air, resulting in an ambient room air-entrained aerosol spray for inhalation by the user, as will be further discussed below. In some implementations, liquid particles in the aerosol flow may be further atomized by an impingement member either before, or contemporaneously with, entrainment of a flow of ambient room air, as will also be further discussed below The cap 40 is connected to the jar 20 to define an inner chamber 42 inside the nebulizer. The cap 40 and jar 20 may be configured to detachably connect to each other. In some implementations, the cap 40 includes a cap fastener 41 configured to securely engage a jar fastener 29 of the jar 20. The cap fastener 41 may include cap threads and the jar fastener 29 may include jar threads that engage the cap threads to provide a threaded engagement of the cap 40 to the jar 20. For instance, a proximal end of the surrounding wall 21 of the jar 20 may include jar threads to threadedly engage corresponding cap threads provided on an annular connection collar 43 extending from a distal end of the cap 40. In other implementations, the cap fastener 41 may include a flange and the jar fastener 29 may include a protrusion, or vice versa, such that the flange and protrusion are configured to matingly engage each other in order to provide a snap-fit securement of the cap 40 to the jar 20.

The cap comprises an entrainment port 44 extending into the inner chamber 42 and configured to act as an inlet for the flow of ambient room air; an entrainment chimney 46 located within the inner chamber 42 and configured to provide an entrainment pathway for the flow of ambient room air to be entrained in the aerosol flow; and an aerosol port 56 configured to removably attach to a user interface, such as a mouthpiece or mask, for delivering the ambient room air-entrained aerosol spray to the user. The chimney includes a first opening 46A in fluid communication with the entrainment port 44 and a second opening 46B in fluid communication with the inner chamber 42. Each of the entrainment port 44, the entrainment chimney 46, and the aerosol port 56, may be generally tubular.

The entrainment port 44 is configured to serve as an inlet port for the flow of ambient room air into the inner chamber 42, as well as an outlet port for discharging an exhalation flow of the user. In some implementations, a secondary flow path separate from the entrainment flow path may be included so that exhalation by the user can flow therethrough either due to a lower resistance to exhalation flow or due to a valve element in communication with the secondary flow path. Moreover, the entrainment port 44 is configured to detachably connect to various breathing circuit accessories, such as PEEP valves and filters. More particularly, an outer diameter of the entrainment port 44 may be approximately 15 mm in order to accept such breathing circuit accessories.

Figure 1:
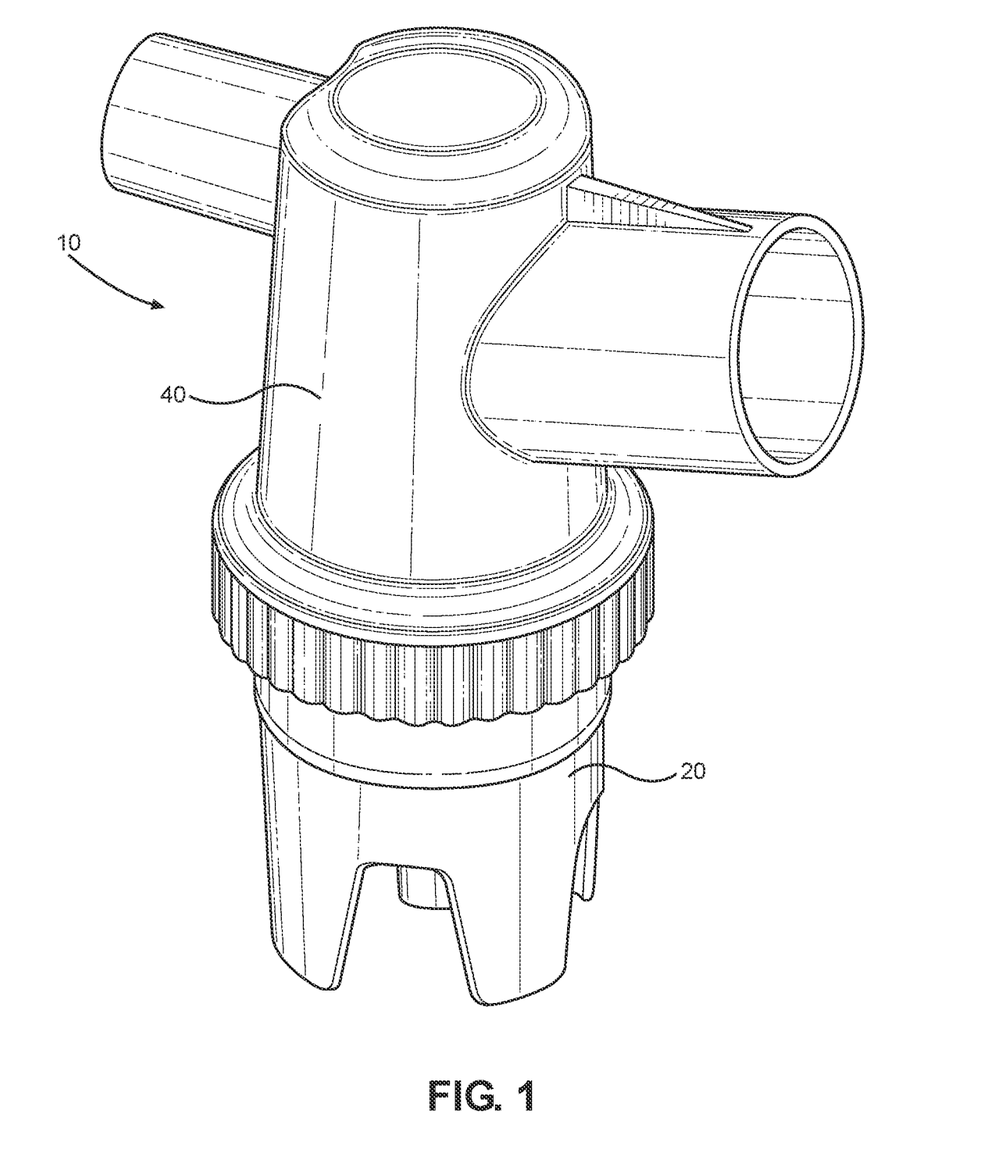
FIG. 1 is a perspective view illustrating an apparatus in accordance with one or more embodiments of the present disclosure.
Figure 2:
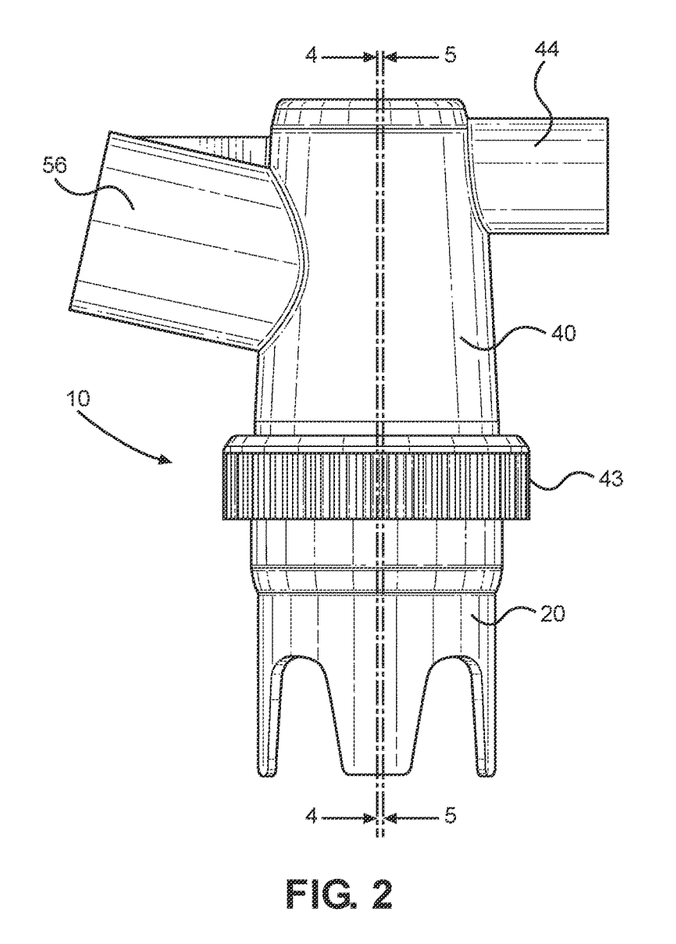
FIG. 2 is a side elevation view illustrating the apparatus of FIG. 1.
Figure 3:
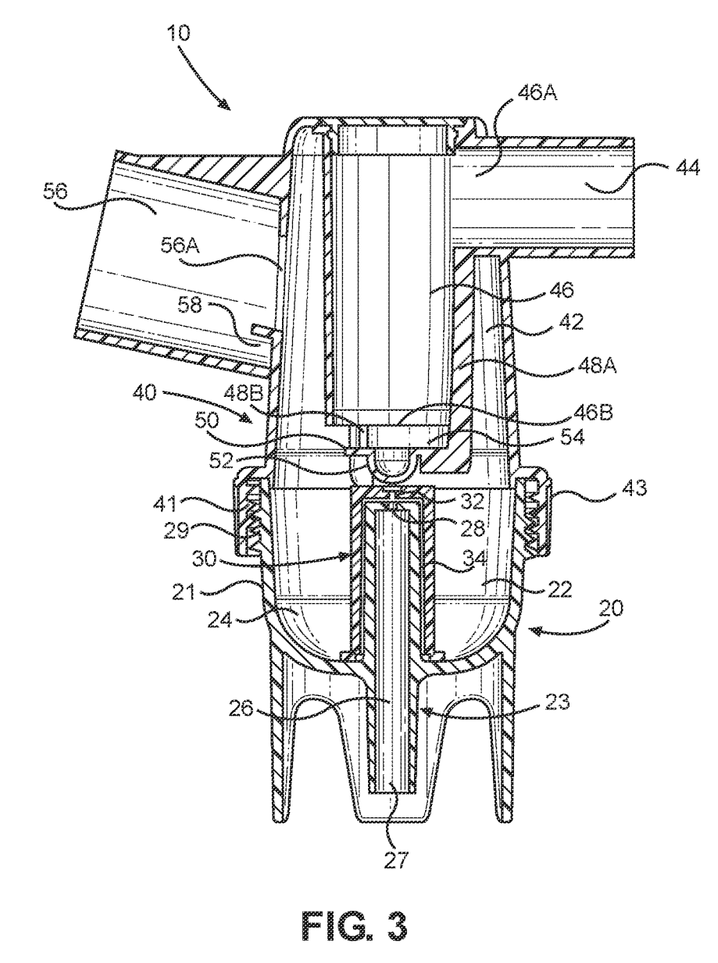
FIG. 3 is a cross-sectional view illustrating the apparatus of FIG. 2 in one or more additional embodiments of the present disclosure.
Figure 3A:
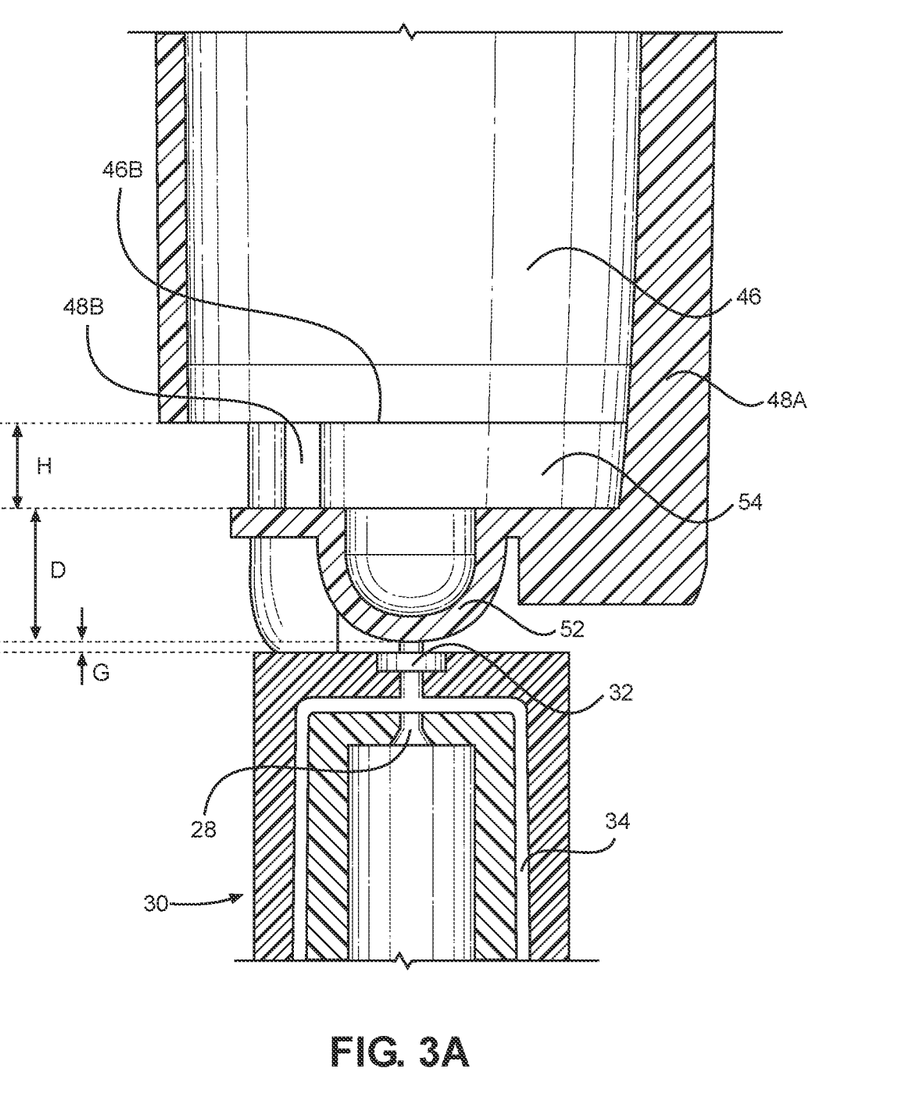
FIG. 3a is an enlarged view of a section of the apparatus shown in FIG. 3.
Figure 4:
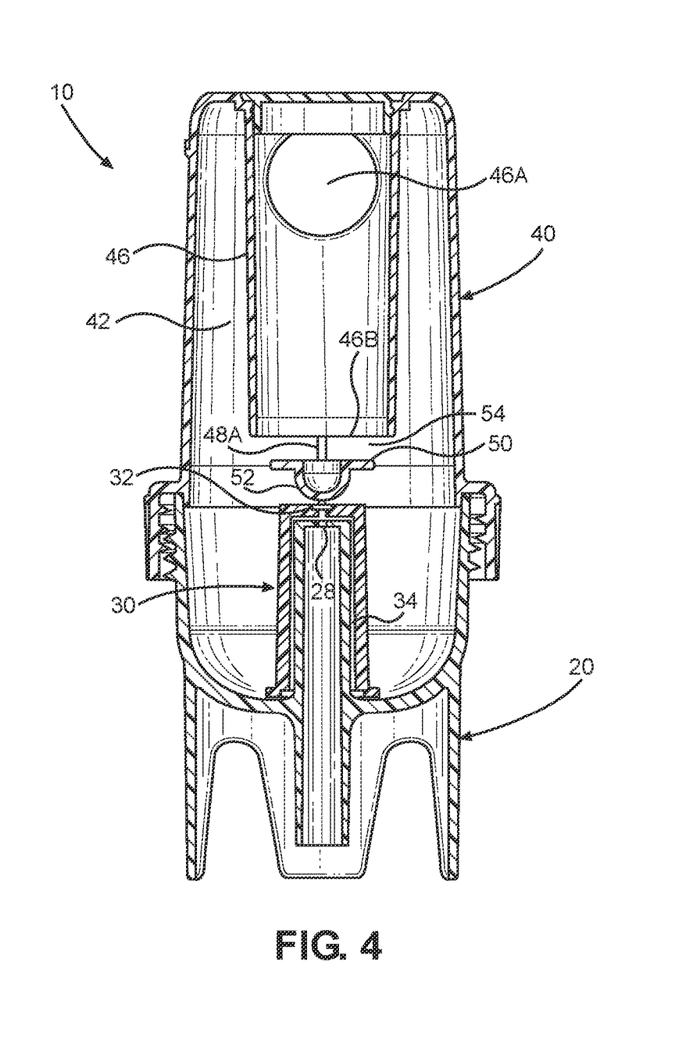
FIG. 4 is a cross-sectional view illustrating the apparatus of FIG. 2 along lines 4-4.
Figure 5:
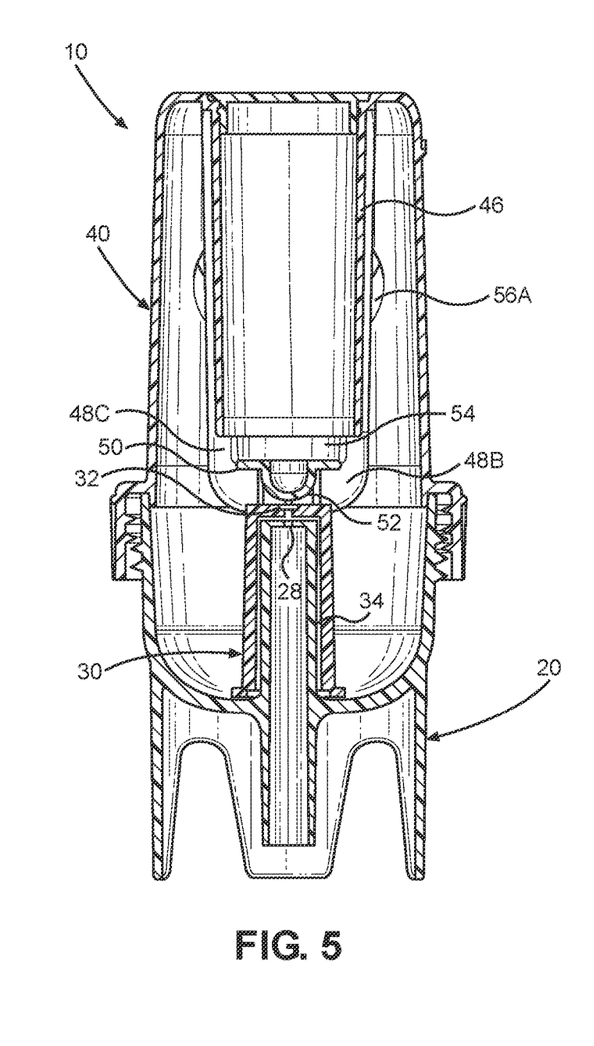
FIG. 5 is a cross-sectional view illustrating the apparatus of FIG. 2 along lines 5-5.

The cap 40 also comprises a deflector base 50, such as a disk or baffle, spaced below the second opening 46B of the entrainment chimney 46. The deflector base 50 is supported by at least one support fin, and may be supported by a plurality of support fins, such as three support fins 48A, 48B, 48C, as illustrated in FIGS. 4 and 5. Each support fin 48A, 48B, 48C may extend from the entrainment chimney 46, a surrounding wall of the cap 40, or a combination of both. In some implementations, the plurality of support fins 48A, 48B, 48C may be equally spaced apart radially around a circumference of the entrainment chimney 46 or the surrounding wall of the cap 40.

The cap 40 further comprises an impingement member 52 extending from the center of the deflector base 50 in a direction toward the jet orifice 32. The impingement member 52 may be dome-shaped, and is configured to prevent a user's exhalation from driving liquid medication out of the nebulizer through the entrainment chimney 46 by partially blocking the second opening 46B. The dome may have a radius of approximately 0.125 inches. The apex of the dome may be spaced a predetermined distance D away from the deflector base 50, where D may be approximately 0.18 inches. This arrangement helps prevent liquid from spraying out of the nebulizer via the entrainment flow path and onto the user's hands or face. Additionally, a longitudinal axis of the entrainment port 44 is arranged substantially perpendicular to a longitudinal axis of the entrainment chimney 46 to provide additional protection from deleterious effects, such as spitting liquid out of the nebulizer via the entrainment flow path, by re-directing the user's exhalation through the entrainment port 44 and away from the user.

As previously described, the liquid medication 24 and the compressed gas form an aerosol flow as they are dispersed from the jet orifice 32 during operation of the nebulizer. The jet orifice 32 is adjacent to and aligned with the center of the impingement member 52 to allow liquid particles in the aerosol flow to impinge the surface of the impingement member 52, thereby further atomizing the particles in the aerosol flow. The jet orifice 32 and the center of the impingement member 52 may be spaced apart by a predetermined distance G, where G may be approximately 0.010 inches, such that aerosol flow discharged from the jet orifice 32 strikes the curved surface of the dome-shaped impingement member, thus forming an aerosol flow with respirable aerosol particles having an aerodynamic diameter between 1 and 5 micrometers for targeted lower airway deposition in a user's lungs.

At least one entrainment vent 54 is spaced between the deflector base 50 and the second opening 46B of the entrainment chimney 46. In implementations having a plurality of support fins 48A, 48B, 48C, a plurality of entrainment vents 54 are correspondingly provided between the deflector base 50 and the second opening 46B of the entrainment chimney 46, such that each entrainment vent 54 is disposed between adjacent support fins. Each entrainment vent 54 is configured to rapidly entrain the ambient room air supplied through the entrainment chimney 46 into the aerosol flow to form the ambient air-entrained aerosol spray for inhalation by the user.

During use, compressed gas at high pressure enters the nebulizer 10 at the compressed gas inlet 27 and travels into the compressed gas passage 26. The compressed gas flowing through the gas passage 26 is converted to a high-speed gas as it flows through the gas outlet 28. This high-speed gas passes through a portion of the fluid flow passage 34 and into the jet orifice 32, thus creating a vacuum that draws the liquid medication 24 from the reservoir 22 through the fluid flow passage 34 and into the jet orifice 32, where the liquid medication mixes with the compressed gas. As previously described, this combined flow of liquid medication 24 and compressed gas is then discharged out of the jet orifice 32 as the aerosol flow. Replacement liquid medicament 22 is continuously drawn up through the fluid flow passage 34 from the reservoir 22 as liquid medicament is aerosolized by the high-pressure gas through the jet orifice 32. Contact of the aerosol flow with the impingement member 52 further atomizes particles in the aerosol flow within the inner chamber 42.

Additionally, the venturi effect created at the gas outlet 28 and the jet orifice 32 also pulls the external ambient room air into the inner chamber 42 via the entrainment pathway defined by the entrainment port 44 and the entrainment chimney 46. This ambient room air is drawn into the inner chamber 42 of the nebulizer for entrainment into the aerosol flow in order to increase the nebulization speed, and therefore enhance treatment time or speed of delivery of the resulting ambient air-entrained aerosol spray to a user. The ambient room air is automatically drawn into the inner chamber 42 through the entrainment flow pathway of the entrainment port 44 and the entrainment chimney 46 due to the pressure differential created between the inner chamber 42 of the nebulizer and the external ambient room air caused by the venturi effect. Accordingly, the user does not have to expend additional effort while breathing to enhance the flow of ambient room air into the nebulizer 10.

Each entrainment vent 54 is located near the jet orifice 32 and is dimensioned such that the aforementioned venturi effect automatically pulls in a flow of the ambient room air to be entrained in the aerosol flow for enhancing the overall rate of nebulization. If the entrainment vent 54 is too large, then the ambient room air will not be automatically pulled into the nebulizer via the venturi effect. Conversely, if the entrainment vent 54 is too small, exhalation by the user could be difficult, and a deleterious accumulation of fluid may occur which could result in the loss of medication. The deflector base 50 is therefore spaced from the second opening 46B of the entrainment chimney 46 by a predetermined distance H in order to increase the nebulization speed, while also resulting in room air-entrained aerosol particles having an aerodynamic diameter between 1 and 5 micrometers. To ensure particles in the room air-entrained aerosol spray have an aerodynamic diameter between 1 and 5 micrometers, the height H of each entrainment vent is greater than 0 inches and less than or equal to about 0.45 inches. In some implementations, each entrainment vent 54 has a height H of approximately 0.12 inches in order to ensure that the ambient room air is rapidly entrained due to the venturi created from the jar, while still resulting in particles of the aerosol spray having an aerodynamic diameter between 1 and 5 micrometers. To further ensure that the ambient room air is rapidly entrained into the aerosol flow, the second opening 46B of the entrainment chimney 46 may have diameter of about 0.59 inches and a cross-sectional area of approximately 0.27 square inches, and the entrainment port 44 may have a diameter of about 0.52 inches and a cross-sectional area of approximately 0.21 square inches.

Each entrainment vent 54 is disposed adjacent to the impingement member 52 and open in a direction transverse to the longitudinal axis of the entrainment chimney 46. This allows the ambient room air to be entrained in the aerosol flow produced at the impingement member and also to be directed toward an opening 56A at the outer periphery of the inner chamber 42 for rapid delivery through the aerosol port 56 for inhalation by the user. In some implementations in which the nebulizer is configured to be used continuously during both inhalation and exhalation by the user, the aerosol port 56 may include a saliva catch 58 located therein and configured to collect any saliva emanating from the user's mouth during inhalation or exhalation in order to prevent contaminating the liquid medicine 24 held in the reservoir 22 of the nebulizer.

Entraining the ambient room air into the aerosol flow within the inner chamber 42 of the nebulizer increases the speed of delivery of the resulting ambient room air-entrained aerosol spray discharged through the aerosol port 56 to the user. More particularly, entrainment of ambient room air into the aerosol flow formed at the impingement member 52 causes the resulting room air-entrained aerosol spray to accelerate toward the aerosol port 56 for inhalation by the user, thus rapidly delivering respirable medication to the user. Additionally, the ambient room air is entrained into the aerosol flow without requiring user effort to enhance the flow of air into the nebulizer.

As previously described, the resultant aerodynamic diameter of the room air-entrained aerosol particles that are discharged through the aerosol port 56 to the user is between 1 and 5 micrometers, which is the ideal respirable range for targeted lower airway deposition in the lungs. While entrainment of the ambient room air into the aerosol flow increases the speed of delivery of the resulting room air-entrained aerosol spray through the aerosol port 56 for inhalation by the user, the location of the deflector base 50 relative to the second opening 46B of the entrainment chimney 46 and location of the impingement member 52 relative to the jet orifice 32 prevent the aerosol spray from entering the entrainment flow path and spraying out of the entrainment port 44 of the nebulizer. The ability of the nebulizer 10 to rapidly nebulize liquid medication while still maintaining a beneficial particle size distribution can help lower the treatment time for a user and thus also lessen the amount of time that a caregiver spends with the user during treatments, thereby improving clinical workflow efficiency. A quicker treatment time also results in better user compliance since less time is needed to hold the nebulizer 10 during use.

The many features and advantages of the disclosure are apparent from the detailed specification, and thus, it is intended by the appended claims to cover all such features and advantages of the disclosure which fall within the true spirit and scope of the disclosure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

What is claimed is:

1. A nebulizer comprising:
   a reservoir configured to hold a liquid medication;
   a jet configured to receive a pressurized gas flow;

a fluid flow passage in fluid communication with the reservoir;

an inner chamber in fluid communication with the reservoir;

an entrainment port in fluid communication with the inner chamber, the entrainment port configured to receive ambient air therethrough;

a chimney in fluid communication with the entrainment port, the chimney extending below the entrainment port, the chimney defining a longitudinal axis that intersects a top end and a bottom end of the chimney, wherein a longitudinal wall of the chimney extends along the longitudinal axis of the chimney, and the entrainment port extends through the longitudinal wall of the chimney;

a vent in fluid communication with the inner chamber and the chimney;

a second port in fluid communication with the inner chamber, the second port configured to receive a user interface, and oriented on an opposite side of the nebulizer from the entrainment port;

a compressed gas passage including a gas outlet, the fluid flow passage being positioned between the gas outlet of the compressed gas passage and a jet orifice of the jet, the jet orifice being positioned downstream of the gas outlet of the compressed gas passage and an outlet of the fluid flow passage; and wherein the pressurized gas flow through the jet is configured to cause ambient air to be drawn through the vent and into the inner chamber.

2. The nebulizer of claim 1, wherein the pressurized gas flow through the jet is configured to create a pressure differential between the inner chamber and an external ambient environment causing ambient air to be drawn through the vent and into the inner chamber via the venturi effect; and wherein the nebulizer is configured to continuously nebulize and atomize the liquid medication during inhalation and exhalation of a user of the nebulizer.

3. The nebulizer of claim 1, wherein the nebulizer is configured to continuously nebulize and atomize the liquid medication during inhalation and exhalation of a user of the nebulizer, wherein the entrainment port is configured to receive ambient air therethrough along a first flow path, and wherein the chimney defines a second flow path through the chimney that is perpendicular to the first flow path.

4. The nebulizer of claim 1, further comprising a secondary flow path separate from a flow path out the entrainment port and into an external ambient environment, and wherein exhalation by a user flows along the secondary flow path.

5. The nebulizer of claim 1, further comprising:
an impingement member positioned above and aligned with the jet, wherein particles in an aerosol flow are atomized by being impinged against the impingement member; and
wherein the impingement member is positioned below the vent and has a height.

6. The nebulizer of claim 5, wherein the height of the vent is greater than 0 inches and less than or equal to 0.45 inches.

7. The nebulizer of claim 5, further comprising:
a deflector base positioned below the vent and above the impingement member; and
the chimney in fluid communication with the entrainment port, and wherein the height of the vent is defined between the deflector base and the longitudinal wall of the chimney.

8. The nebulizer of claim 7, wherein the longitudinal wall of the chimney is positioned farther away from the jet than the deflector base.

9. The nebulizer of claim 5, wherein the impingement member is dome shaped and has a radius, and
wherein the nebulizer is configured to continuously nebulize and atomize the liquid medication during inhalation and exhalation of a user of the nebulizer.

10. The nebulizer of claim 1, further comprising:
a cap that comprises the entrainment port; and
a jar removably coupled to the cap, the jar comprising the reservoir, and wherein the cap and the jar collectively define the inner chamber.

11. A nebulizer comprising:
a reservoir configured to hold a liquid medication;
a fluid flow passage in fluid communication with the reservoir;
an inner chamber in fluid communication with the reservoir;
an entrainment port in fluid communication with the inner chamber, the entrainment port configured to receive ambient air therethrough;
a jet configured to receive a pressurized gas flow, the jet having a jet orifice positioned at an end of the jet,
a compressed gas passage including a gas outlet, the fluid flow passage being positioned between the gas outlet of the compressed gas passage and the jet orifice of the jet, the jet orifice being positioned downstream of the gas outlet of the compressed gas passage and an outlet of the fluid flow passage;
a chimney in fluid communication with the port, the chimney extending below the port, the chimney defining a longitudinal axis that intersects a top end and a bottom end of the chimney, wherein a longitudinal wall of the chimney extends along the longitudinal axis of the chimney, and the entrainment port extends through the longitudinal wall of the chimney;
a vent in fluid communication with the inner chamber and the chimney;
a second port in fluid communication with the inner chamber, the second port configured to receive a user interface, and oriented on an opposite side of the nebulizer from the entrainment port;
wherein the pressurized gas flow through the gas outlet and through the jet is configured to create a vacuum that draws liquid medication along the fluid flow passage and through the jet orifice along with the pressurized gas flow to generate an aerosol flow, wherein the pressurized gas flow through the jet is configured to cause ambient air to be drawn through the port and into the inner chamber; and
wherein the cross-section of the jet orifice is larger than the cross-section of the gas outlet upstream of the jet orifice.

12. The nebulizer of claim 11, wherein the nebulizer is configured to continuously nebulize and atomize the liquid medication during inhalation and exhalation of a user of the nebulizer, and
The entrainment port is configured to provide an inhalation pathway for inhalation through the entrainment port and an exhalation pathway for exhalation out of the nebulizer through the entrainment port and into an ambient environment.

13. The nebulizer of claim 11, further comprising:
a saliva catch that extends into the second port; and
wherein the second port is configured to direct aerosolized liquid therethrough.

14. The nebulizer of claim 11, wherein the entrainment port is configured to receive ambient air therethrough along a first flow path and further comprising:

the chimney in fluid communication with the entrainment port, the chimney defining a second flow path through the chimney that is perpendicular to the first flow path, and wherein the nebulizer is configured to continuously nebulize and atomize the liquid medication during inhalation and exhalation of a user of the nebulizer.

15. A nebulizer comprising:

a reservoir configured to hold a liquid medication;

a jet configured to receive pressurized gas;

an inner chamber in fluid communication with the reservoir;

a port in fluid communication with the inner chamber, the port configured to receive ambient air therethrough;

a chimney in fluid communication with the port, the chimney extending below the port, the chimney defining a longitudinal axis that intersects a top end and a bottom end of the chimney, wherein a longitudinal wall of the chimney extends along the longitudinal axis of the chimney, and the entrainment port extends through the longitudinal wall of the chimney;

the nebulizer is configured to continuously nebulize and atomize the liquid medication during inhalation and exhalation of a user of the nebulizer, the port is configured to provide an inhalation pathway for inhalation through the port and an exhalation pathway for exhalation out of the nebulizer through the port and into an ambient environment, the port is configured to receive ambient air therethrough along a flow path, the port being an entrainment port, a longitudinal axis of the entrainment port is not parallel to a longitudinal axis of the chimney;

a vent in fluid communication with the inner chamber and the chimney; and a second port in fluid communication with the inner chamber, the second port configured to receive a user interface, and oriented on an opposite side of the nebulizer from the entrainment port.

16. The nebulizer of claim 15, wherein the flow path is a first flow path, and wherein the chimney defines a second flow path through the chimney that is perpendicular to the first flow path.

17. The nebulizer of claim 16, further comprising:

an impingement member, wherein particles in an aerosol flow are atomized by being impinged against the impingement member;

a deflector base positioned above the impingement member; and the vent positioned above the impingement member, the deflector base, and the jet, a height of the vent is defined between the longitudinal wall of the chimney and the deflector base.

18. The nebulizer of claim 16, wherein the longitudinal axis of the entrainment port is perpendicular to the longitudinal axis of the chimney.

19. The nebulizer of claim 15, wherein the second port is configured to direct aerosolized liquid therethrough, and wherein the second port is angled relative to the entrainment port.

20. The nebulizer of claim 19, further comprising a saliva catch positioned within the second port.

21. The nebulizer of claim 1, wherein the entrainment port is positioned on a first side of the nebulizer and further comprising:

wherein the longitudinal wall of the chimney is positioned between the entrainment port and the second port.

22. The nebulizer of claim 1, wherein the vent is open in a direction transverse to the longitudinal axis of the chimney.

23. The nebulizer of claim 1, further comprising:

an impingement member aligned with the jet, wherein aerosol particles are configured to impinge upon a surface of the impingement member to further atomize the aerosol particles;

a deflector base coupled to and extending from the impingement member towards the longitudinal wall of the chimney, the longitudinal wall of the chimney being positioned closer to the second port than the entrainment port; and wherein the deflector base does not extend past the longitudinal wall of the chimney.

* * * * *